(12) United States Patent
Song et al.

(10) Patent No.: US 10,281,416 B2
(45) Date of Patent: May 7, 2019

(54) DEVICES FOR USE IN SOLID-STATE NMR ANALYSIS

(71) Applicant: Waters Technologies Corporation, Milford, MA (US)

(72) Inventors: Xiangjin Song, Westborough, MA (US); Jonathan Belanger, Whitinsville, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 932 days.

(21) Appl. No.: 14/813,625

(22) Filed: Jul. 30, 2015

(65) Prior Publication Data

US 2016/0033599 A1 Feb. 4, 2016

Related U.S. Application Data

(60) Provisional application No. 62/032,790, filed on Aug. 4, 2014.

(51) Int. Cl.
*G01N 24/08* (2006.01)
*G01R 33/30* (2006.01)

(52) U.S. Cl.
CPC .............. *G01N 24/08* (2013.01); *G01R 33/30* (2013.01); *G01R 33/307* (2013.01)

(58) Field of Classification Search
CPC ....... G01N 24/08; G01R 33/30; G01R 33/307
See application file for complete search history.

(56) References Cited

U.S. PATENT DOCUMENTS

| | | | | |
|---|---|---|---|---|
| 3,742,226 A * | 6/1973 | Smallbone | ......... | G01N 23/2204 250/432 R |
| 5,202,633 A * | 4/1993 | Doty | .................... | G01R 33/307 324/321 |
| 5,298,864 A * | 3/1994 | Muller | .................... | G01R 33/31 324/315 |
| 5,325,059 A * | 6/1994 | Doty | .................... | G01R 33/307 324/321 |
| 5,754,048 A * | 5/1998 | Bielecki | ............... | G01R 33/307 324/321 |
| 5,760,586 A * | 6/1998 | Foerster | ............... | G01R 33/307 324/318 |
| 6,583,622 B1 * | 6/2003 | Hills | ...................... | G01R 33/30 324/307 |
| 6,686,740 B2 * | 2/2004 | Tschirky | ............... | G01R 33/307 324/318 |
| 6,812,706 B2 * | 11/2004 | Leung | ................... | G01R 33/307 324/318 |
| 7,352,179 B2 * | 4/2008 | Chen | ..................... | G01N 24/08 324/303 |
| 7,436,181 B2 * | 10/2008 | Krahn | .................. | G01R 33/307 324/318 |

(Continued)

*Primary Examiner* — Dixomara Vargas
(74) *Attorney, Agent, or Firm* — Womble Bond Dickinson (US) LLP; Deborah M. Vernon; Heath T. Misley

(57) ABSTRACT

The present disclosure relates to devices and methods for use in SSNMR analysis of solid particulate samples. These devices and methods are configured to contain a solid particulate sample as it undergoes SSNMR analysis while also operating to attenuate peak broadening in the resulting spectrum due to anisotropic dipole coupling interactions and CSA during such analysis by generating a substantially fluidized bed of the solid particulate sample.

9 Claims, 13 Drawing Sheets

(56) References Cited

U.S. PATENT DOCUMENTS

| | | | | |
|---|---|---|---|---|
| 7,718,135 B2* | 5/2010 | Himmelsbach | | G01R 33/307 324/308 |
| 7,750,636 B2* | 7/2010 | Shiino | | G01R 33/307 324/318 |
| 8,106,657 B2* | 1/2012 | Sakellariou | | G01R 33/307 324/307 |
| 8,203,339 B2* | 6/2012 | Johannessen | | G01D 5/145 324/307 |
| 8,212,559 B2* | 7/2012 | Armbruster | | G01R 33/307 324/307 |
| 8,409,807 B2* | 4/2013 | Neely | | G01N 24/08 435/6.12 |
| 8,563,298 B2* | 10/2013 | Lowery, Jr. | | C12Q 1/6895 422/68.1 |
| 8,883,423 B2* | 11/2014 | Neely | | G01N 24/08 435/6.12 |
| 9,046,493 B2* | 6/2015 | Neely | | G01N 24/08 |
| 9,063,060 B2* | 6/2015 | Inukai | | G01N 24/08 |
| 9,279,869 B2* | 3/2016 | Shinagawa | | G01R 33/30 |
| 9,360,457 B2* | 6/2016 | Neely | | G01N 24/08 |
| 9,488,648 B2* | 11/2016 | Neely | | B82Y 25/00 |
| 9,551,769 B2* | 1/2017 | Fordham | | G01R 33/4818 |
| 9,588,067 B2* | 3/2017 | Mitchell | | G01N 24/081 |
| 9,644,234 B2* | 5/2017 | Pipper | | B01L 7/52 |
| 9,702,852 B2* | 7/2017 | Lowery, Jr. | | G01N 24/08 |
| 9,714,940 B2* | 7/2017 | Lowery, Jr. | | B82Y 25/00 |
| 9,778,331 B2* | 10/2017 | Hunkeler | | G01R 33/307 |
| 9,903,923 B2* | 2/2018 | Schett | | G01R 33/307 |
| 9,945,654 B2* | 4/2018 | Freytag | | G01R 33/07 |
| 2004/0178793 A1* | 9/2004 | Leung | | G01R 33/307 324/321 |
| 2009/0112119 A1* | 4/2009 | Kim | | A61B 10/0266 600/564 |
| 2013/0088232 A1* | 4/2013 | Inukai | | G01N 24/08 324/321 |
| 2013/0266944 A1* | 10/2013 | Neely | | G01N 24/08 435/6.11 |
| 2014/0312900 A1* | 10/2014 | Ozaku | | G01R 33/307 324/318 |
| 2016/0047867 A1* | 2/2016 | Turcu | | G01R 33/305 324/321 |

* cited by examiner

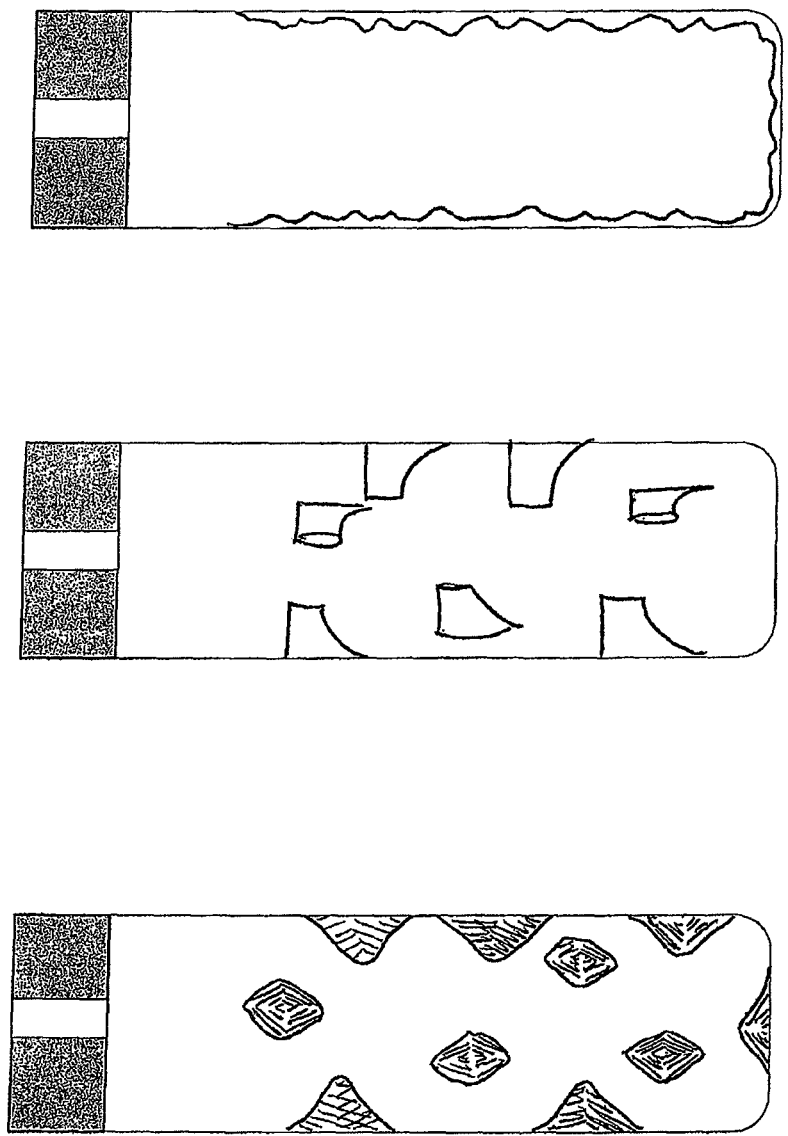

Fig. 6A
Fig. 6B
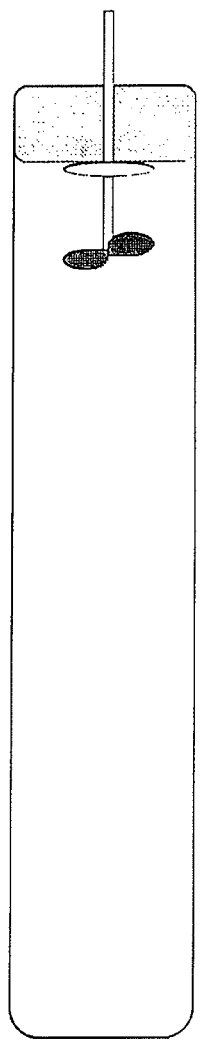
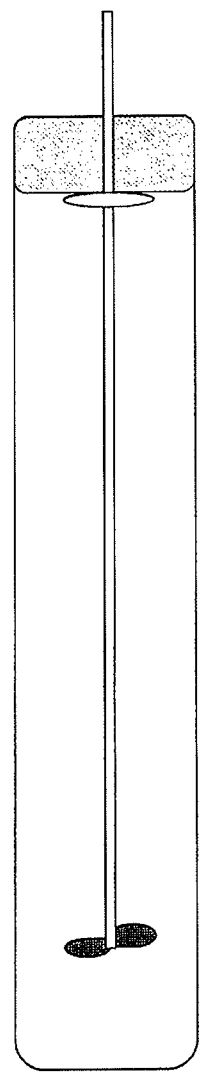

DEVICES FOR USE IN SOLID-STATE NMR ANALYSIS

CROSS-REFERENCE

This application claims priority to U.S. Provisional Application No. 62/032,790 filed Aug. 4, 2014, which is incorporated herein by reference in its entirety.

TECHNICAL FIELD

The present disclosure relates to devices for use in solid-state nuclear magnetic resonance (SSNMR) analysis of solid particulate samples.

BACKGROUND

Nuclear magnetic resonance (NMR) is a physical phenomenon in which certain atomic nuclei in the presence of an applied, external magnetic field absorb and re-emit electromagnetic radiation. This phenomenon is harnessed in NMR spectroscopy, one of the most powerful analytical techniques for determining the composition and structure of materials. In NMR spectroscopy, radio frequency (RE) pulses are irradiated into a sample of material positioned in a strong, static magnetic field, followed by measurement of the electromagnetic response of the sample. This measurement is used to generate a spectrum of one or more lines representing the resonant frequency or frequencies of the target nucleus (e.g., $^1H$) relative to a standard (i.e., the chemical shift(s)). The position, number, and size of chemical shifts are indicative of the relative positions/electronic environments of the target nuclei in a material and are diagnostic of the structure of the material.

NMR spectroscopy has been more successfully used in the analysis of liquids or materials dissolved in solvents than of solids. The basic problem in NMR spectroscopy of solids is that the rapid molecular tumbling and diffusion (i.e., Brownian motion) present in liquids and solutions that averages out anisotropic dipole coupling interactions and chemical shift anisotropy (CSA), the main causes of line broadening in NMR spectroscopy, is not present in solids. Thus, the lines in NMR spectra of solid samples are typically broad and unresolved, oftentimes tens to hundreds of ppm in width. In many instances, the line broadening is so severe that lines having different chemical shifts cannot be readily discerned from each other.

"Magic Angle" Spinning (MAS) is the most widely used technique developed to attenuate the line broadening that occurs from anisotropic dipole coupling interactions and CSA during NMR spectroscopy of solids. While not true isotropic motion, MAS involves spinning the sample extremely rapidly along a fixed axis at the "Magic Angle" (i.e., 54.74°) with respect to the direction of the externally applied magnetic field, $B_0$. Complicated multiple pulse programs are another approach used, often in conjunction with MAS (i.e., combined rotation and multiple-pulse spectroscopy—CRAMPS), to decouple anisotropic dipole coupling interactions and CSA. However, while substantial improvements in spectrum resolution are generally obtained from using MAS NMR, either alone or in the combination with multiple-pulse programs, these techniques have so far been unable to generate NMR spectra having resolutions comparable to those seen in spectra of liquids or solutions.

Decoupling of anisotropic dipole coupling interactions using MAS requires, at a minimum, that the spinning frequency of the sample be higher than the homonuclear dipolar coupling frequency of the target nuclei. This presents substantial technological challenges, especially when the homonuclear dipolar coupling frequency is very large. For example, since the dipolar coupling of $^1H$ is greater than 100 kHz, its decoupling would require that the sample container be spun at an even higher spinning frequency. Likewise for CSA. While most CSA effects can be effectively attenuated by MAS at frequencies of from 6 to 10 kHz, CSA effects can be more pronounced in stronger magnetic fields, thus requiring even higher MAS spinning frequencies. However, very few MAS NMR spectrometers are technically capable of such ultra-fast spinning frequencies, with most spectrometers only capable of spinning frequencies of 20 to 25 kHz or less. Moreover, even those that have such capability still produce NMR spectra of inferior resolution to those produced from the analysis of samples in a liquid or solvated phase.

SUMMARY OF THE INVENTION

The present disclosure relates to devices and methodologies for use in SSNMR analysis of solid particulate samples. In general and according to certain embodiments, the devices of the present disclosure are configured to contain a solid particulate sample as it undergoes SSNMR analysis while also operating to attenuate peak broadening in the resulting spectrum due to anisotropic dipole coupling interactions and CSA during such analysis.

One embodiment of the present disclosure is directed to a device for attenuating peak broadening during NMR analysis of a solid particulate sample. The device comprises a sample container having an inner wall and sized to hold the solid particulate sample, a motor, a non-magnetic, electrically non-conductive drive shaft having a first end and a second end, and a non-magnetic, electrically non-conductive impeller. The motor is fixably attached to the first end of the non-magnetic, electrically non-conductive drive shaft. The non-magnetic, electrically non-conductive impeller is fixably attached to the second end of the non-magnetic, electrically non-conductive drive shaft. The non-magnetic, electrically non-conductive impeller is located inside the sample container.

Another embodiment of the present disclosure is directed to a device for attenuating peak broadening during NMR analysis of a solid particulate sample. The device comprises a sample container sized to hold the solid particulate sample, a motor, a first and a second non-magnetic, electrically non-conductive drive shaft, each having a first end and a second end, and a non-magnetic, electrically non-conductive impeller. The motor is located at a distance from the sample container such that a magnetic field strength of a NMR magnet used to analyze the solid particulate sample in the sample container is about 0.5 millitesla or less. The motor is fixably attached to the first end of the first non-magnetic, electrically non-conductive drive shaft. The first end of the second non-magnetic, electrically non-conductive drive shaft is fixably attached to the second end of the first non-magnetic, electrically non-conductive drive shaft through a transmission gear box. The non-magnetic, electrically non-conductive impeller is fixably attached to the second end of the second non-magnetic, electrically non-conductive drive shaft and is located inside the sample container.

Another embodiment of the present disclosure is directed to a device for attenuating peak broadening during NMR analysis of a solid particulate sample. The device comprises a sample container sized to hold the solid particulate sample, a motor located at a distance from the sample container, a first and a second non-magnetic, electrically non-conductive drive shaft, each having a first end and a second end, and a non-magnetic, electrically non-conductive impeller. The distance between the motor and the sample container is selected such that substantially no disruption is caused to NMR analysis of the solid particulate sample. The motor is fixably attached to the first end of the first non-magnetic, electrically non-conductive drive shaft. The first end of the second non-magnetic, electrically non-conductive drive shaft is fixably attached to the second end of the first non-magnetic, electrically non-conductive drive shaft through a transmission gear box. The non-magnetic, electrically non-conductive impeller is fixably attached to the second end of the second non-magnetic, electrically non-conductive drive shaft and is located inside the sample container.

Another embodiment of the present disclosure is directed to a method for attenuating peak broadening in NMR analysis of a solid particulate sample. The method comprises at least three steps. The first step of the method comprises providing a sample container with the solid particulate sample. The second step of the method comprises mixing the solid particulate sample with a non-magnetic, electrically non-conductive impeller rotated at a rate to generate a substantially fluidized bed of solid particulates. An air-driven motor is used to rotate the non-magnetic, electrically non-conductive impeller. The third step of the method comprises performing NMR analysis on the fluidized bed of solid particulates.

Another embodiment of the present disclosure is directed to a method for attenuating peak broadening in NMR analysis of a solid particulate sample. The method comprises at least three steps. The first step of the method comprises providing a sample container with the solid particulate sample. The second step of the method comprises mixing the solid particulate sample with a non-magnetic, electrically non-conductive impeller rotated at a rate to generate a substantially fluidized bed of solid particulates. A motor is used to rotate the non-magnetic, electrically non-conductive impeller and is located at a distance from the sample container such that a magnetic field of a NMR spectrometer used to analyze the solid particulate sample in the sample container is about 0.5 millitesla or less. The third step of the method comprises performing NMR analysis on the fluidized bed of solid particulates.

The above embodiments can include one or more of the following features. In some embodiments, the motor can be non-magnetic, electrically non-conductive and/or gas-driven. In other embodiments, the motor can be magnetic and/or electrically-driven and is either (1) located at a distance from the sample container corresponding to a magnetic field strength of a corresponding NMR magnet of about 0.5 millitesla or less or (2) shielded from the NMR magnet, wherein the shielding may be active or passive. In some embodiments, the non-magnetic, electrically non-conductive shaft can be flexible or rigid. In some embodiments, the non-magnetic, electrically non-conductive shaft comprises carbon-filled PEEK. In some embodiments, the non-magnetic, electrically non-conductive impeller can comprise a ceramic material and/or a polymer. In some embodiments, the inner wall of the sample container comprises one or more protruding structures dimensioned and configured to impede any vortex generated by the spinning of the impeller without preventing the generation of a substantially fluidized bed of solid sample particulates. In some embodiments, the one or more protruding structures comprise baffles and/or fins protruding from the inner wall at randomly spaced intervals.

In some embodiments, the inner wall of the sample container comprises undulations and/or ripples. In some embodiments, the transmission gear box can be a 90 degree transmission gear box. In some embodiments, the motor can rotate the non-magnetic, electrically non-conductive impeller at a rate to generate a substantially fluidized bed of the solid particulate sample.

The embodiments of the present disclosure provide advantages over the prior art based on their unique configurations and performance properties. For example, in order to decouple the homonuclear dipolar coupling of the target nuclei using MAS, the spinning frequency of the sample be higher than the dipolar coupling frequency. This is a substantial technological hurdle, particularly in instances where the homonuclear dipolar coupling frequency is very large, since the vast majority of MAS NMR spectrometers are incapable of achieving such ultra-fast spinning frequencies. In contrast, the devices of the present disclosure are configured to generate a substantially fluidized bed of a solid particulate sample in the sample container as it undergoes SSNMR analysis, which better approximates the random, Brownian motion of a liquid or solvated sample compared to MAS. Thus, the anisotropic dipole coupling interactions and CSA during such analysis are averaged out, which operates to attenuate any peak broadening in the resulting spectrum.

BRIEF DESCRIPTION OF THE DRAWINGS

The foregoing and other features and advantages provided by the present disclosure will be more fully understood from the following description of exemplary embodiments when read together with the accompanying drawings.

FIGS. 5A, 5B, 5C, 5D, 5E, and 5F depict cross-sections of the sample container component of the devices of the present invention where the sample container is capped with a plug cap and has various shaped protrusions extending from their inner walls or an undulated/rippled surface of their inner walls.

FIGS. 6A and 6B depict cross-sections of the sample container component of the devices of the present invention where the sample container is capped with a plug cap and exhibit variable positioning of the non-magnetic, electrically non-conductive impeller and integration of a flange on the non-magnetic, electrically non-conductive drive shaft.

DETAILED DESCRIPTION

In various aspects, configurations, and embodiments, the present disclosure provides devices that, by generating a substantially fluidized bed of a solid particulate sample, attenuate peak broadening due to anisotropic dipole coupling interactions and CSA during SSNMR analysis of the sample, as well as methods of using such devices in SSNMR analysis of solid particulate samples. In other aspects, configurations, and embodiments, the present disclosure provides methods that attenuate peak broadening in SSNMR analysis by generating a substantially fluidized bed of solid particulates.

As used herein, the term "non-magnetic" refers to materials that are neither ferromagnetic (i.e., permanent magnets or capable of becoming a permanent magnet) nor measurably paramagnetic (i.e., magnetic when in the presence of an applied external magnetic field). Examples of such non-magnetic materials include, but are not limited to, non-magnetic metals and alloys, ceramics, and plastics. Examples of such non-magnetic metals and alloys include, but are not limited to, copper and stainless steel. Examples of such ceramics include, but are not limited to, boron nitride and zirconia. Examples of such plastics include, but are not limited to, polychlorotrifluoroethylene, polytetrafluoroethylene, polyimides, polymethylmethacrylate, PEEK (polyether ether ketone), and polyoxymethylene.

As used herein, the term "electrically non-conductive" refers to materials that are not measurably conductive of electricity. Examples of such non-magnetic materials include, but are not limited to, ceramics and plastics. Examples of such ceramics include, but are not limited to, boron nitride and zirconia. Examples of such plastics include, but are not limited to, polychlorotrifluoroethylene, polytetrafluoroethylene, polyimides, polymethylmethacrylate, PEEK (polyether ether ketone), and polyoxymethylene.

As used herein, the term "fixably attached" refers to two structures or components that are connected to each other, but that can also be disconnected, as opposed to being permanently affixed to each other.

As used herein, the term "fluidized bed" refers to the solid particulate/gas mixture formed from the introduction of a pressurized gas through the solid particulate sample such that the mixture takes on characteristics of a fluid. The gas used should not contain nuclei detectable by the NMR technique employed (e.g., $^1H$, $^{13}C$, etc.). Examples of such gases include, but are not limited to, air, nitrogen, and the noble gases.

Figure 1:
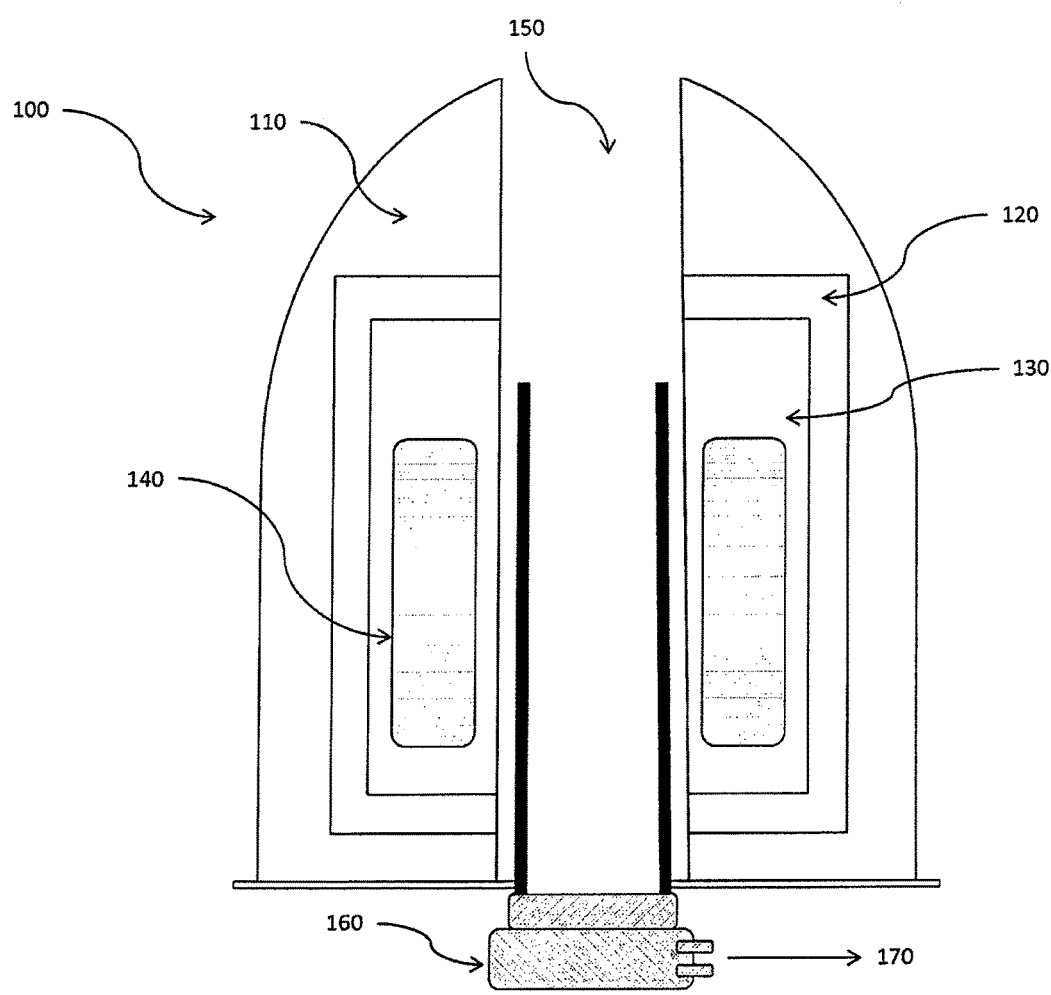
FIG. 1 depicts a cross-section of a conventional, modern NMR spectrometer.

In general, all modern NMR spectrometers have the same basic components, as illustrated in FIG. 1. NMR spectrometer 100 includes a vacuum chamber 110 that surrounds a liquid nitrogen chamber 120, which in turn surrounds a liquid helium chamber 130. A superconducting solenoid 140 is located within liquid helium chamber 130. A cylindrical bore 150 travels through the center of vacuum chamber 110, liquid nitrogen chamber 120, liquid helium chamber 130, and superconducting solenoid 140. An NMR probe 160 is inserted into the bottom of bore 150. During NMR spectroscopy analysis, a sample container (i,e., an NMR tube or rotor) containing the material to be analyzed is inserted downward through the top of bore 150 into probe 160. The sample is irradiated with RF pulses delivered via RF coils in NMR probe 160 in the presence of a strong, static magnetic field generated by superconducting solenoid 140. These RF pulses generate an additional, temporary magnetic field orthogonal to the static magnetic field. The temporary magnetic field applies a torque to the nuclear spins of the target nuclei of the sample, twisting them out of alignment with the static magnetic field, generating electromagnetic signals 170. The electromagnetic signals 170 generated are detected by NMR probe 160 and sent to a console and then host computer, where they are converted into an NMR spectrum.

All of the devices of the present invention are designed and configured to be used with the conventional NMR spectrometers described above and, at a minimum, comprise (1) a sample container sized to hold the solid particulate sample, (2) a motor, (3) at least one non-magnetic, electrically non-conductive drive shaft having a first end and a second end, and (4) a non-magnetic, electrically non-conductive impeller located inside the sample container, wherein the motor is fixably attached to the first end of the non-magnetic, electrically non-conductive drive shaft and the non-magnetic, electrically non-conductive impeller is fixably attached to the second end of the non-magnetic, electrically non-conductive drive shaft. The sample container, non-magnetic, electrically non-conductive drive shaft, and, where applicable, motor components of the devices of the present invention are all sized to be inserted into the bore of such NMR spectrometers. The sample container and non-magnetic, electrically non-conductive drive shaft components of the devices of the present invention are also all sized to be inserted into the NMR probe when it is positioned in the bottom of the bore of such NMR spectrometers.

Figure 2A:
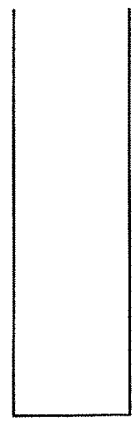
FIG. 2A depicts a cross-section of the sample container component of the devices of the present invention where the sample container is flat-bottomed.
Figure 2B:
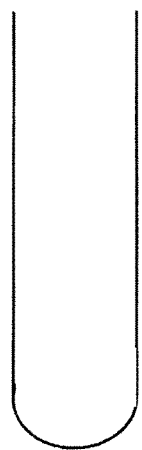
FIG. 2B depicts a cross-section of the sample container component of the devices of the present invention where the sample container is round-bottomed.
Figure 3A:
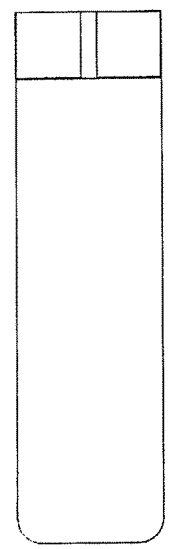
FIG. 3A depicts a cross-section of the sample container component of the devices of the present invention where the sample container is capped with a plug cap.
Figure 3B:
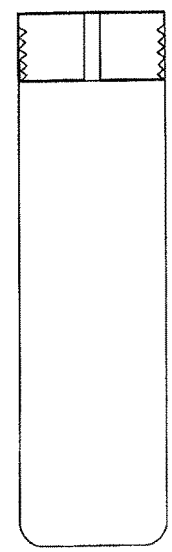
FIG. 3B depicts a cross-section of the sample container component of the devices of the present invention where the sample container is capped with a screw cap.

The sample container component of the devices of the present invention is fabricated from a non-magnetic material, as defined above, and is hollow cylindrical in shape, having a sealed bottom and an open top. The sealed bottom of the sample container can be flat or rounded, as illustrated in FIGS. 2A and 2B, respectively. In certain embodiments, the sample container component of the devices of the present invention can be constructed from a conventional SSNMR sample container having an open top and bottom, wherein the bottom opening of the conventional SSNMR sample container is sealed with a removable cap fabricated from a non-magnetic material as defined above. The open top of the sample container, when charged with a solid particulate sample, is sealed with a removable cap, also fabricated from a non-magnetic material as defined above. In certain embodiments, the sample container, including the cap, is fabricated from a ceramic, such as boron nitride or zirconia, or a plastic, such as polychlorotrifluoroethylene (e.g., Kel-F® from 3M Company, Neoflon® from Daikin), polytetrafluoroethylene (e.g., Teflon® from E.I. DuPont de Nemours and Company Corporation), polyimides (e.g., Vespel® from E.I. DuPont de Nemours and Company Corporation), polymethylmethacrylate, PEEK (polyether ether ketone), polyoxymethylene, or any combination thereof. In certain embodiments, the sample container can be sealed with the cap by either plugging or screwing the cap into the open top, as illustrated in FIGS. 3A and 3B, respectively. In the embodiment where the cap is screwed into the open top, both the cap (male) and the interior of the open top (female) are threaded.

The caps are dimensioned and configured to provide for a cylindrical hole passing from the top surface through to the bottom surface of the cap. The cylindrical hole is sized to allow for the non-magnetic, electrically non-conductive drive shaft to pass through the cap and into the hollow interior of the sample container. In certain embodiments, the cross-sectional width of the cylindrical hole can be 2, 1.5, 1, 0.5, 0.25, or 0.1 mm. The sample container, in combination with the cap, is sized to fit into the both the bore and NMR probe of an NMR spectrometer. In certain embodiments, the length of the sample container can be 15, 14, 13, 12, 11, 10, 9, 8, 7, 6, or 5 mm. In certain embodiments, the cross-sectional width of the sample container can be 5, 4, 3, 2, 1, or 0.5 mm.

Figure 4:
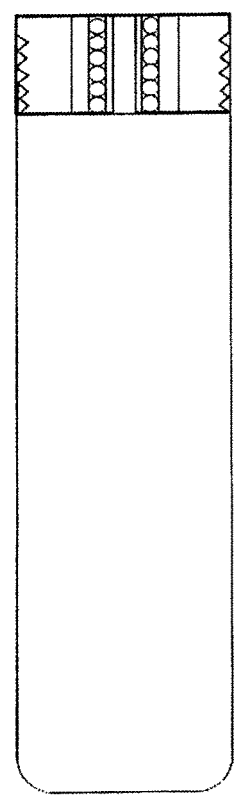
FIG. 4 depicts a cross-section of the sample container component of the devices of the present invention where the sample container is capped with a screw cap into which a ball bearing system has been integrated.
Figure 5A:
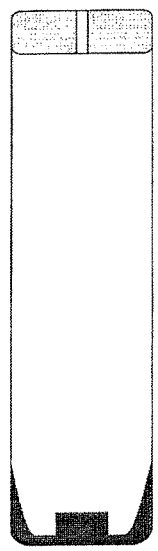
Figure 5B:
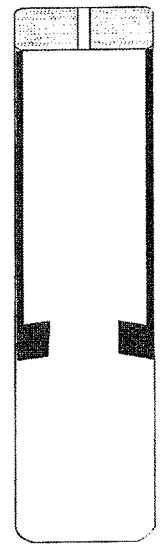
Figure 5C:
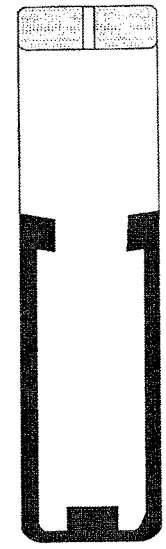

In certain embodiments, a bearing system can be integrated into the cylindrical hole through the cap in order to reduce friction between the non-magnetic, electrically non-conductive drive shaft and the cap, thereby mitigating the generation of excessive amounts of heat. Examples of bearing systems that can be used include, but are not limited to, sleeve bearings, linear bearings, tapered bearings, ball bearings, and roller bearings. A sample container fitted with a removable screw cap having an integrated ball bearing system is illustrated in FIG. 4.

The hollow interior of the sample container is sized to hold a solid particulate sample. In certain embodiments, the hollow interior of the sample container comprises one or more structures designed and configured to impede the vortex generated by the spinning of the impeller and, thus, randomly redirect the solid particulates so as to better approximate the Brownian motion that occurs in liquid and solution NMR samples. The one or more structures can be of any shape and/or size sufficient to impede the vortex generated by the spinning of the impeller without preventing the generation of a substantially fluidized bed of solid sample particulates. Examples of such structures include, but are not limited to, fins and baffles that protrude from the inner wall of the sample container at randomly spaced intervals. In certain embodiments, the transition between the protrusions and the inner wall of the same container are smooth and curved so as to prevent accumulation of solid sample particulates in the regions inside the sample container where the protrusion connects to the inner wall. In certain embodiments, the random redirection of solid particulates can be achieved if the inner wall of the sample container is undulated or rippled. In certain embodiments, these protrusions, undulations, and ripples can either be integrated into the inner wall of the sample container or positioned in the hollow interior of the sample container using inserts made of non-magnetic material. Various examples of capped sample containers with inner wall protrusions are illustrated in FIGS. 5A, 5B, 5C, 5D, 5E, and 5F, respectively.

The motor of the present invention can be fabricated from magnetic and/or non-magnetic, electrically non-conductive materials. In certain embodiments, the motor is gas-driven or electrically-driven. The gas-driven motors are powered by supplying a gas or mixture of gasses to the motor. The gas or gas mixture is supplied to an inlet on the motor via a first hose and is removed from an outlet on the motor via a second hose. The gas or gas mixture can be supplied to the motor from an electrically-driven pressure-regulated air compressor or from a pressure-regulated reservoir (i.e., tank) of a compressed gas, such as air or nitrogen. Examples of air-driven motors that can be used in the present invention include, but are not limited to, those manufactured by Huco Dynatork and by Micro Motors, Inc. The electrically-driven motors can be powered via alternating current or direct current (i.e., battery powered). Examples of electrically-driven motors that can be used in the present invention include, but are not limited to, overhead stirrers conventionally used in laboratories, brushed electric motors, and high torque mini electric DC geared motors.

The motor component of the devices of the present invention are capable of driving the non-magnetic, electrically non-conductive drive shaft, and, thus, rotating the non-magnetic, electrically non-conductive impeller at a rate sufficient to generate a substantially fluidized bed of the solid particulate sample. Examples of such rates include, but are not limited to, 50, 100, 150, 200, 250, 300, 350, 400, 450, 500, 550, 600, 650, 700, 750, 800, 850, 900, 950, 1000, 1500 2000, 2500, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 55,000, 60,000, 65,000, 70,000, 75,000, 80,000, 85,000, 90,000, and 100,000 rpms.

Figure 7:
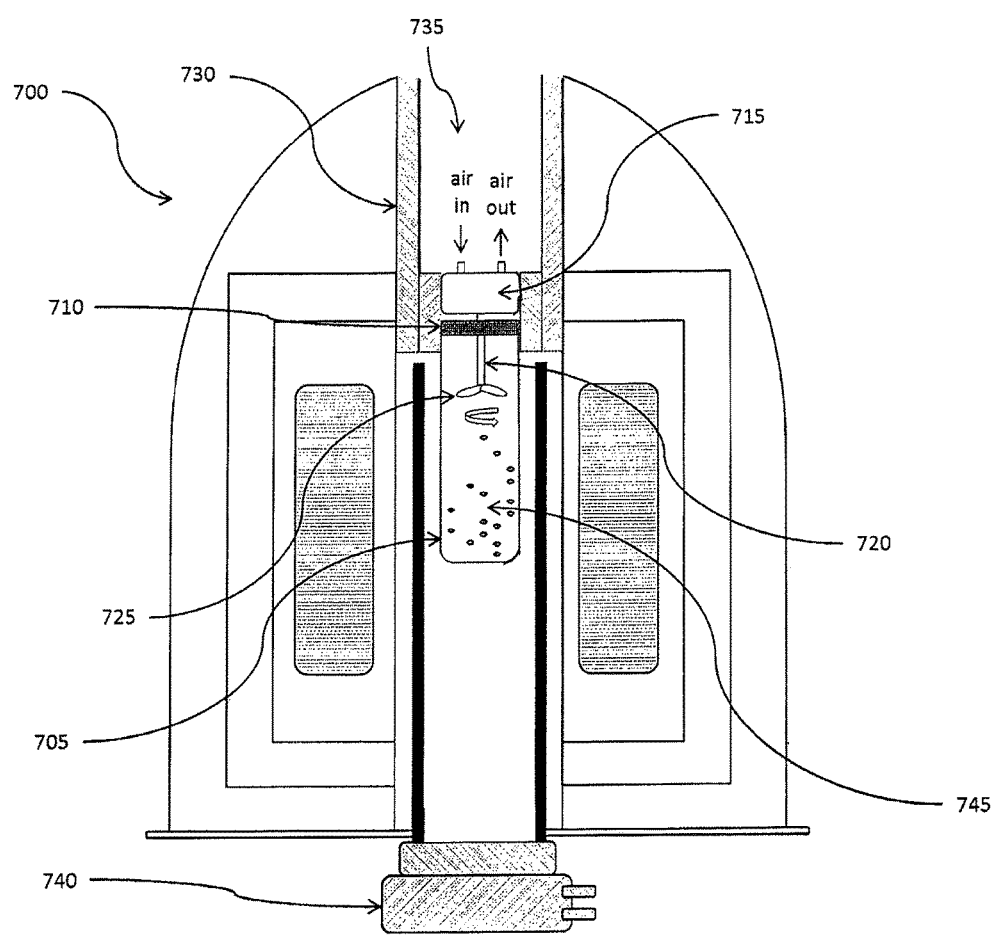
FIG. 7 depicts a cross-section of a device according to the present invention where the motor is air-driven.
Figure 8:
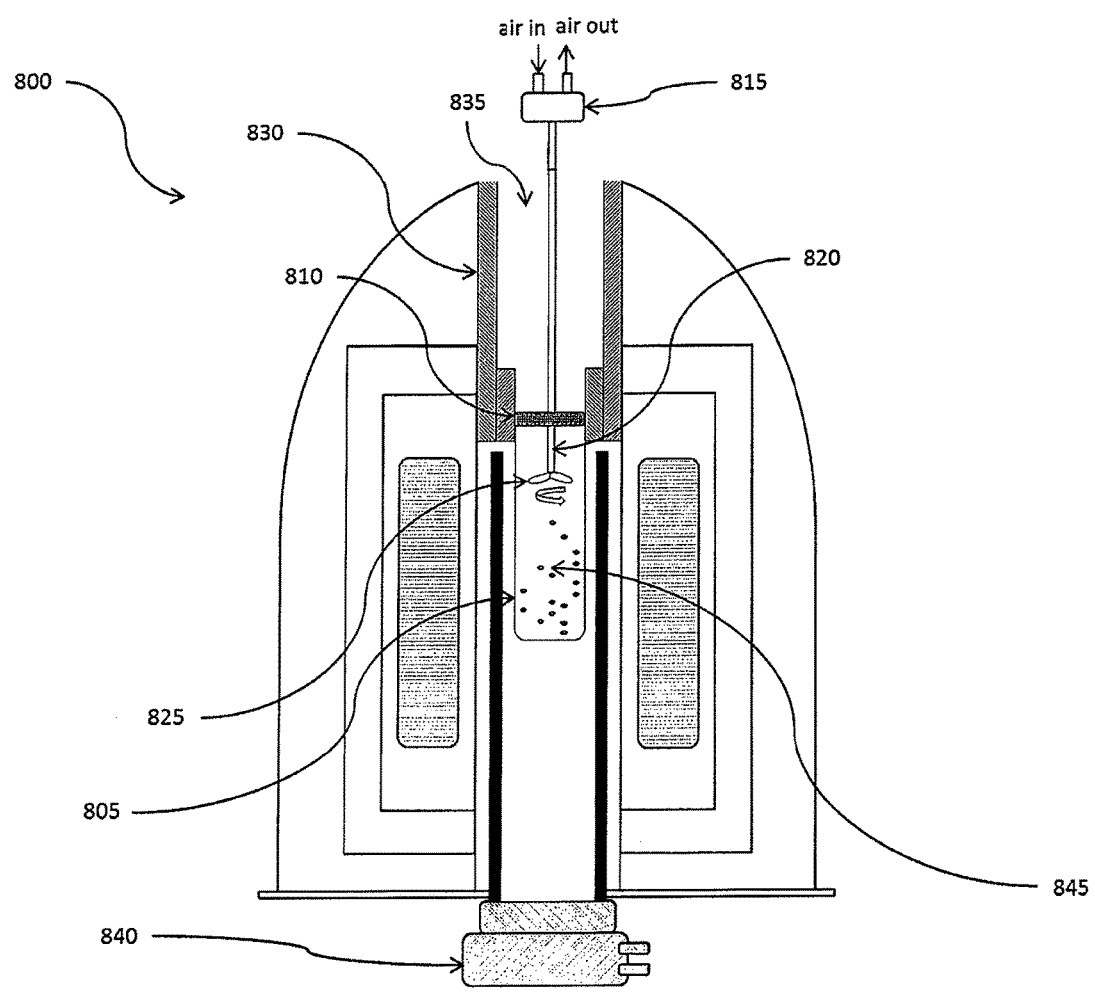
FIG. 8 depicts a cross-section of a device according to the present invention where the motor is air-driven.

Examples of devices according to the present invention where the motor is air-driven are illustrated in FIGS. 7 and 8.

In FIG. 7, device 700 having a sample container 705 fitted with a plug cap 710, an air-driven motor 715, a non-magnetic, electrically non-conductive drive shaft 720, and a non-magnetic, electrically non-conductive impeller 725. Non-magnetic, electrically non-conductive drive shaft 720 is connected at one end to air-driven motor 715 and at the other end to non-magnetic, electrically non-conductive impeller 725 and traverses through plug cap 710. Non-magnetic, electrically non-conductive impeller 725 is located in sample container 705. Air is pumped into and expelled out of air-driven motor 715. This drives non-magnetic, electrically non-conductive drive shaft 720, which, in turn, rotates non-magnetic, electrically non-conductive impeller 725 at a speed sufficient to generate a substantially fluidized bed of the solid particulate sample 745. Device 700 is inserted into bore 735, with the sample container 705 portion of device 700 being positioned inside probe 740. Device 700 is held in place by a device rack 730 attached to the inner wall of bore 735.

In FIG. 8, device 800 having a sample container 805 fitted with a plug cap 810, an air-driven motor 815, a non-magnetic, electrically non-conductive drive shaft 820, and a non-magnetic, electrically non-conductive impeller 825. Non-magnetic, electrically non-conductive drive shaft 820 is connected at one end to air-driven motor 815 and at the other end to non-magnetic, electrically non-conductive impeller 825 and traverses through plug cap 810. Due to the length of non-magnetic, electrically non-conductive drive shaft 820, the air-driven motor 815 is located outside of the bore 835. Non-magnetic, electrically non-conductive impeller 825 is located in sample container 805. Air is pumped into and expelled out of air-driven motor 815. This drives non-magnetic, electrically non-conductive drive shaft 820, which, in turn, rotates non-magnetic, electrically non-conductive impeller 825 at a speed sufficient to generate a substantially fluidized bed of the solid particulate sample 845. A portion of device 800 is inserted into bore 835, with the sample container 805 portion of device 800 being positioned inside probe 840. Device 800 is held in place by a device rack 830 attached to the inner wall of bore 835.

If the motor of the present invention is fabricated from magnetic material and/or is electrically driven, either (1) the motor must be located at a distance from the sample container such that the motor functions normally and the magnetic field of the NMR is not perturbed or (2) the motor must be shielded from the NMR magnet Likewise, the same applies if an electrically-driven pressure-regulated air compressor is used to power a gas driven motor. This is because if the motor is too close in proximity to the sample container and, by extension the NMR magnet, during analysis, any magnetic portions of the motor will be attracted to the magnet, leading to undesirable mechanical constraints or heat from induced currents, such that the motor malfunctions and/or is permanently damaged. Furthermore, the operation of motors constructed from magnetic materials could induce a magnetic field, which could perturb the magnetic field of the NMR. In certain embodiments, the motor is located at a distance from the sample container corresponding to a magnetic field strength of a corresponding NMR magnet of about 0.5 millitesla (mT) (i.e., about 5 Gauss (G)) or less.

Shielding of the NMR can be achieved either actively or passively. Active shielding can be achieved by building a second magnet with a field of opposite sign on the outside of the NMR magnet, thereby cancelling any external magnetic field. Passive shielding can be achieved by enclosing either the NMR spectrometer or the motor and/or air compressor in a shielding material that doesn't block the magnetic field, but rather draws the magnetic field into itself, providing a path for the magnetic field lines to travel around the shielded volume. Examples of materials that can be used to fabricate passive shielding include, but are not limited to, steel, Ni—Fe alloys, such as Amumetal™, Permalloy, and Mu-Metal, and nanocrystalline grain structure ferromagnetic metal coatings. It should be noted that proximity of these materials to the magnetic field around the NMR samples may cause perturbation of the NMR magnetic field.

Figure 9:
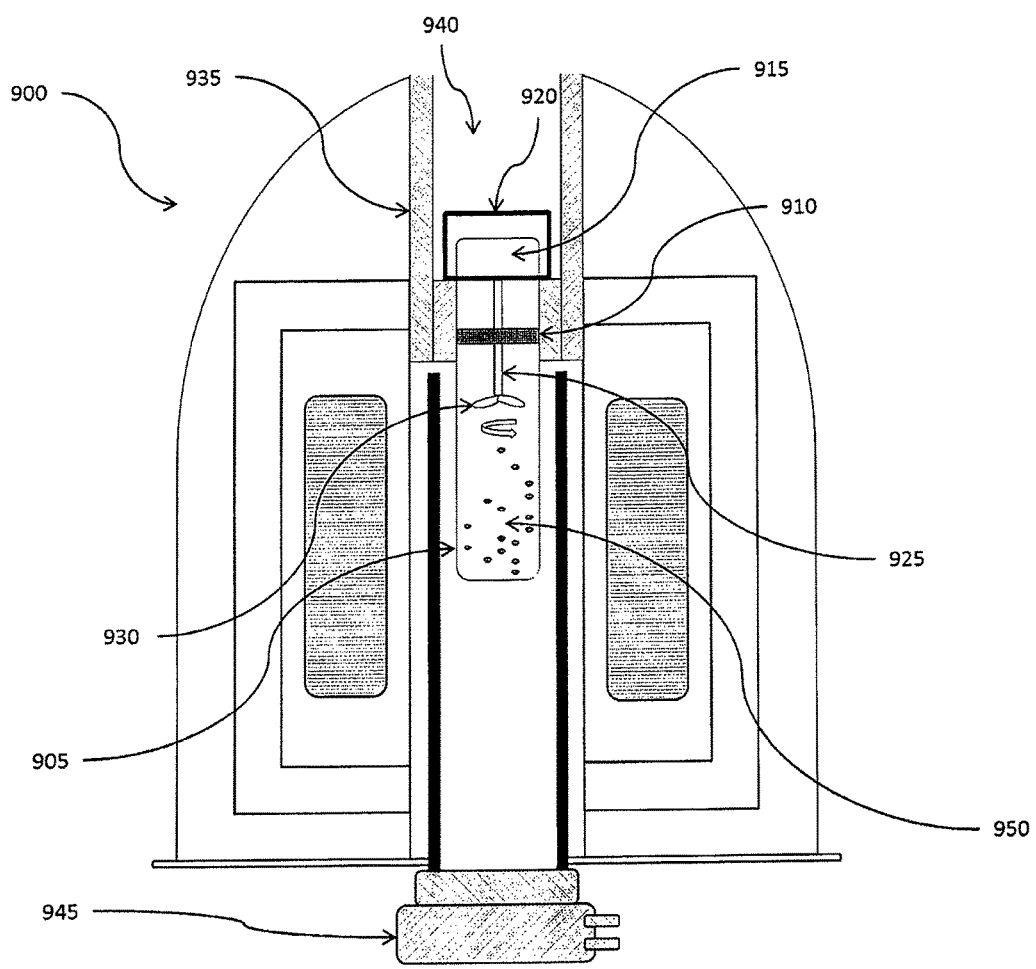
FIG. 9 depicts a cross-section of a device according to the present invention where the motor is electrically-driven and passively shielded.
Figure 10:
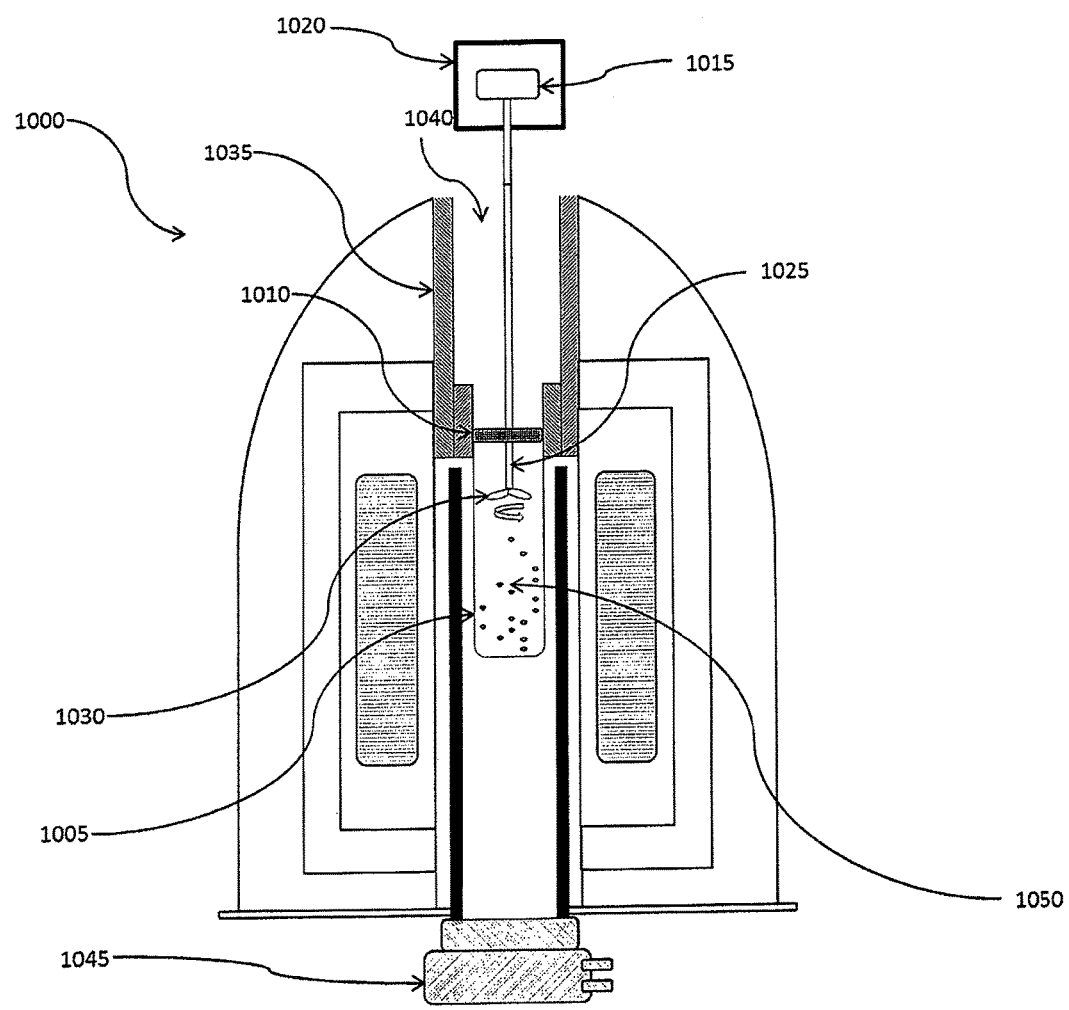
FIG. 10 depicts a cross-section of a device according to the present invention where the motor is electrically-driven and passively shielded.

Examples of devices according to the present invention where the motor is electrically-driven and passively shielded are illustrated in FIGS. 9 and 10.

In FIG. 9, device 900 having a sample container 905 fitted with a plug cap 910, an electrically-driven motor 915, a non-magnetic, electrically non-conductive drive shaft 925, and a non-magnetic, electrically non-conductive impeller 930. Non-magnetic, electrically non-conductive drive shaft 925 is connected at one end to electrically-motor 915 and at the other end to non-magnetic, electrically non-conductive impeller 930 and traverses through plug cap 910. Non-magnetic, electrically non-conductive impeller 930 is located in sample container 905. Electrically-driven motor 915 is battery-powered and encased in a passive shield 920. Electrically-driven motor 915 drives non-magnetic, electrically non-conductive drive shaft 925, which, in turn, rotates non-magnetic, electrically non-conductive impeller 930 at a speed sufficient to generate a substantially fluidized bed of the solid particulate sample 950. Device 900 is inserted into bore 940, with the sample container 905 portion of device 900 being positioned inside probe 945. Device 900 is held in place by a device rack 935 attached to the inner wall of bore 940.

In FIG. 10, device 1000 having a sample container 1005 fitted with a plug cap 1010, an electrically-driven motor 1015, a non-magnetic, electrically non-conductive drive shaft 1025, and a non-magnetic, electrically non-conductive impeller 1030. Non-magnetic, electrically non-conductive drive shaft 1025 is connected at one end to electrically-motor 1015 and at the other end to non-magnetic, electrically non-conductive impeller 1030 and traverses through plug cap 1010. Non-magnetic, electrically non-conductive impeller 1030 is located in sample container 1005. Electrically-driven motor 1015 is battery-powered and encased in a passive shield 1020. Due to the length of non-magnetic, electrically non-conductive drive shaft 1025, electrically-driven motor 1015 is located outside of the bore 1040. Electrically-driven motor 1015 drives non-magnetic, electrically non-conductive drive shaft 1025, which, in turn, rotates non-magnetic, electrically non-conductive impeller 1030 at a speed sufficient to generate a substantially fluidized bed of the solid particulate sample 1050. Device 1000 is inserted into bore 1040, with the sample container 1005 portion of device 1000 being positioned inside probe 1045. Device 1000 is held in place by a device rack 1035 attached to the inner wall of bore 1040.

The non-magnetic, electrically non-conductive drive shaft component of the device of the present invention is fabricated from a non-magnetic, electrically non-conductive material. In certain embodiments, the drive shaft is rigid or flexible. In certain embodiments, the drive shaft is fabricated from a ceramic, such as boron nitride or zirconia, or a plastic, such as polychlorotrifluoroethylene (e.g., Kel-F® from 3M Company, Neoflon® from Daikin), polytetrafluoroethylene (e.g., Teflon® from E.I. DuPont de Nemours and Company Corporation), polyimides (e.g., Vespel® from E.I. DuPont de Nemours and Company Corporation), polymethylmethacrylate, PEEK (polyether ether ketone), polyoxymethylene, or any combination thereof. The drive shaft is cylindrical in shape and has a first end and a second end. In certain embodiments, the length of the drive shaft can be in the range of from 1 to 100 cm. Examples of such lengths include, but are not limited to, 1, 2, 3, 4, 5, 10, 15, 20, 25, 30, 35, 40, 45, 50, 55, 60, 65, 70, 75, 80, 85, 90, 95, 100, 150, 200, 250, 300, 350, 400, 450, or 500 cm long. The cross-sectional width of the drive shaft is sized to enable it to snugly fit through the cylindrical hole or bearing system in the cap with no discernible gap between the drive shaft and the cylindrical hole or bearing system, yet still rotate at high speeds. In certain embodiments, the cross-sectional width of the cylindrical hole can be 2, 1.5, 1, 0.5, 0.25, or 0.1 mm. The first end of the drive shaft is dimensioned and configured to be fixably attached to the motor, while the second end of the drive shaft is dimensioned and configured to be fixably attached to the impeller. The first and second ends can be fixably attached to the motor and impeller, respectively, by any means known in the art. Examples of such means include, but are not limited to, non-magnetic, electrically non-conductive clamps, bolts, and screws, as well as rubber sleeves.

In certain embodiments, two or more non-magnetic, electrically non-conductive drive shafts are used in the devices of the present invention. For example, in one embodiment, the device of the present invention has two non-magnetic, electrically non-conductive drive shafts, each having a first end and a second end. The motor is fixably attached to the first end of the first non-magnetic, electrically non-conductive drive shaft and the non-magnetic, electrically non-conductive impeller is fixably attached to the second end of the second non-magnetic, electrically non-conductive drive shaft. The first end of the second non-magnetic, electrically non-conductive drive shaft is fixably attached to the second end of the first non-magnetic, electrically non-conductive drive shaft through a transmission gear box. In certain embodiments, the transmission gearbox fixably attaches the first and second non-magnetic, electrically non-conductive drive shafts at an angle that is greater than 0 and less than 180 degress. Examples of such angles include, but are not limited to, 5, 10, 15, 20, 25, 30, 35, 40, 45, 50, 55, 60, 65, 70, 77, 80, 85, 90, 95, 100, 105, 110, 115, 120, 125, 130, 135, 140, 145, 150, 155, 160, 165, 170, and 175 degrees.

Figure 11:
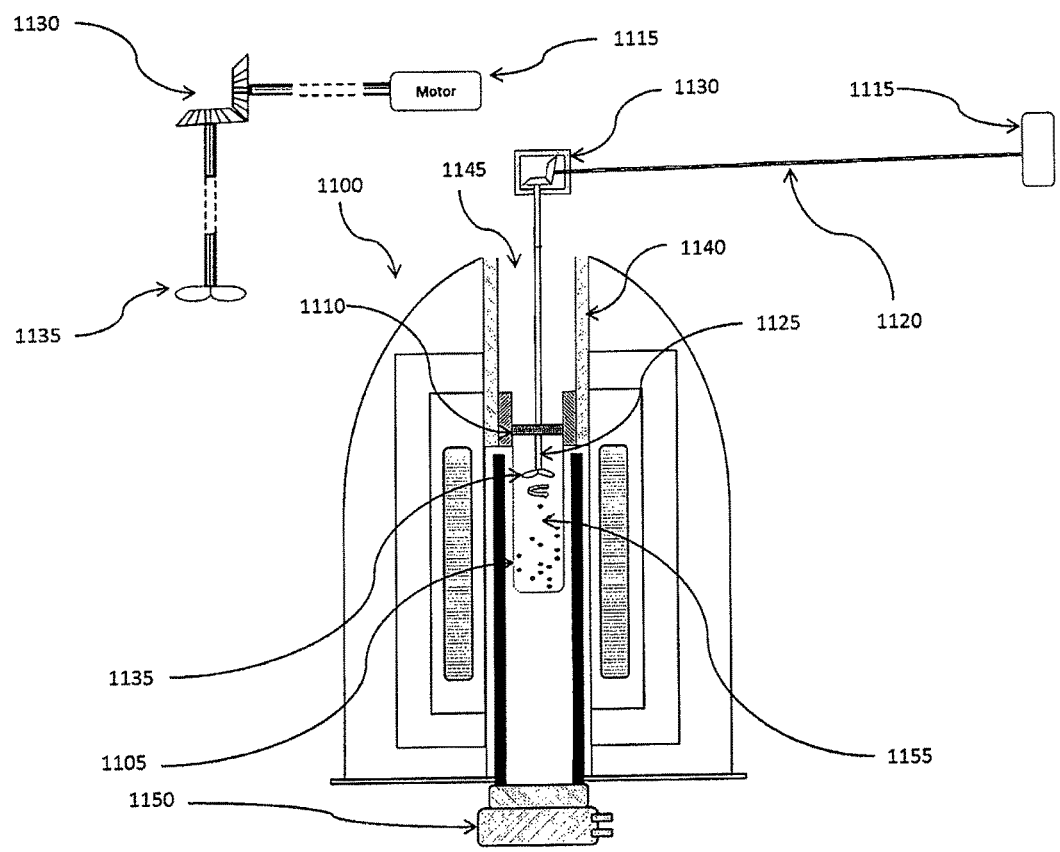
FIG. 11 depicts a cross-section of a device according to the present invention where two or more non-magnetic, electrically non-conductive drive shafts are used.
Figure 12:
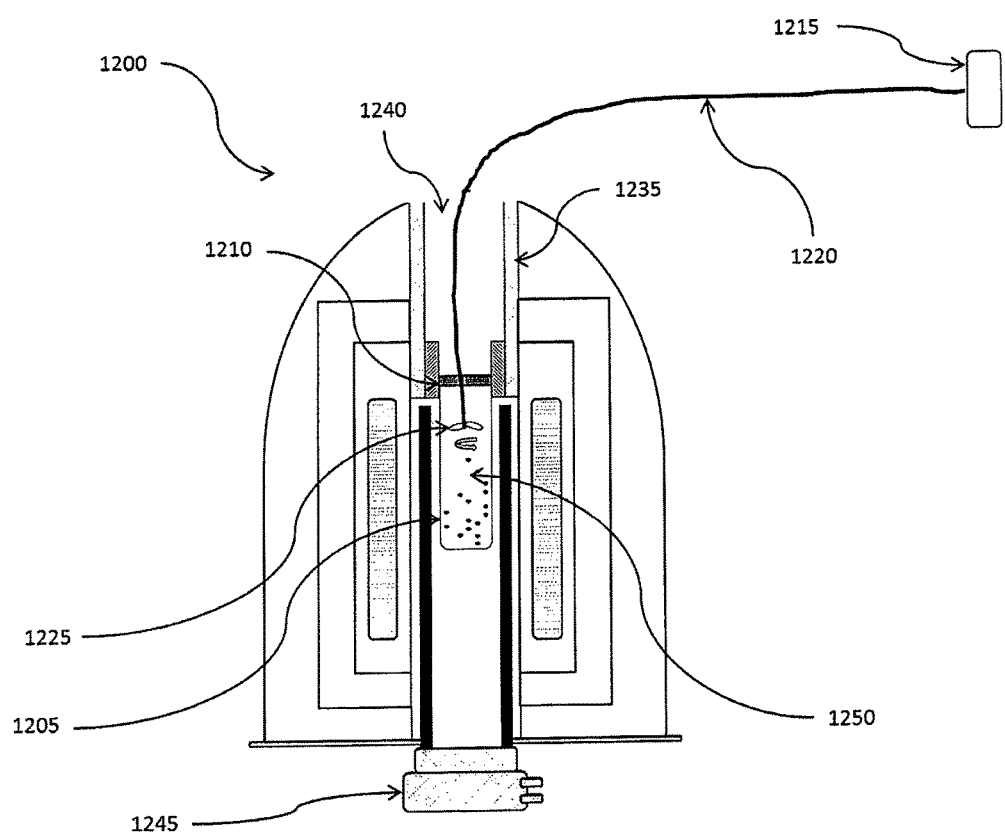
FIG. 12 depicts a cross-section of a device according to the present invention where a flexible non-magnetic, electrically non-conductive drive shaft is used.

Examples of devices according to the present invention where two or more non-magnetic, electrically non-conductive drive shafts or a flexible non-magnetic, electrically non-conductive drive shaft are used are illustrated in FIGS. 11 and 12.

In FIG. 11, device 1100 having a sample container 1105 fitted with a plug cap 1110, an electrically-driven motor 1115, a first non-magnetic, electrically non-conductive drive shaft 1120, a second non-magnetic, electrically non-conductive drive shaft 1125, and a non-magnetic, electrically non-conductive impeller 1135. The first non-magnetic, electrically non-conductive drive shaft 1120 is connected at one end to electrically-driven motor 1115. The second non-magnetic, electrically non-conductive drive shaft 1125 is connected at one end to non-magnetic, electrically non-conductive impeller 1135 and traverses through plug cap 1110. The first and second drive shaft are connected to each other via a transmission gear box 1130. Non-magnetic, electrically non-conductive impeller 1135 is located in sample container 1105. Electrically-driven motor 1115 is AC-powered and located at a distance from the sample container 1105 such that the motor functions normally and the magnetic field of the NMR is not perturbed. Electrically-driven motor 1115 drives non-magnetic, electrically non-conductive drive shafts 1120 and 1125, which, in turn, rotate non-magnetic, electrically non-conductive impeller 1135 at a speed sufficient to generate a substantially fluidized bed of the solid particulate sample 1155. Device 1100 is inserted into bore 1145, with the sample container 1105 portion of device 1100 being positioned inside probe 1150. Device 1100 is held in place by a device rack 1140 attached to the inner wall of bore 1145.

In FIG. 12, device 1200 having a sample container 1205 fitted with a plug cap 1210, an electrically-driven motor 1215, a flexible non-magnetic, electrically non-conductive drive shaft 1220, and a non-magnetic, electrically non-conductive impeller 1225. The flexible non-magnetic, electrically non-conductive drive shaft 1220 is connected at one end to electrically-driven motor 1215 and at the other end to non-magnetic, electrically non-conductive impeller 1225 and traverses through plug cap 1210. Non-magnetic, electrically non-conductive impeller 1225 is located in sample container 1205. Electrically-driven motor 1215 is AC-powered and located at a distance from the sample container 1205 such that the motor functions normally and the magnetic field of the NMR is not perturbed. Electrically-driven motor 1215 drives flexible non-magnetic, electrically non-conductive drive shaft 1220, which, in turn, rotate non-magnetic, electrically non-conductive impeller 1225 at a speed sufficient to generate a substantially fluidized bed of the solid particulate sample 1250. Device 1200 is inserted into bore 1240, with the sample container 1205 portion of device 1200 being positioned inside probe 1245. Device 1200 is held in place by a device rack 1235 attached to the inner wall of bore 1240.

The non-magnetic, electrically non-conductive impeller component of the device of the present invention, like the drive shaft component described above, is fabricated from a non-magnetic, electrically non-conductive material. In certain embodiments, the impeller is fabricated from a ceramic, such as boron nitride or zirconia, or a plastic, such as polychlorotrifluoroethylene (e.g., Kel-F® from 3M Company, Neoflon® from Daikin), polytetrafluoroethylene (e.g., Teflon® from E.I. DuPont de Nemours and Company Corporation), polyimides (e.g., Vespel® from E.I. DuPont de Nemours and Company Corporation), polymethylmethacrylate, PEEK (polyether ether ketone), polyoxymethylene, or any combination thereof. In other certain embodiments, the impeller is fabricated from carbon, e.g., carbon fiber, or glass, e.g., silica glass.

In certain embodiments, the impeller (e.g., 725 in FIG. 7, 825 in FIG. 8, 930 in FIG. 9, 1030 in FIG. 10, 1135 in FIG. 11, 1225 in FIG. 12) can be an axial-flow impeller or a radial flow impeller. In certain embodiments, the impeller is a propeller. In certain embodiments, the impeller is a spiral or screw propeller. The impeller can have two or more blades. In certain embodiments, the impeller has two, three, four, or five blades. The blades can be any shape that facilitates the mixing of the solid particulate sample with the inert gas in the sample container such that a substantially fluidized bed of the solid particulates is formed. Examples of such shapes include, but are not limited to, flat paddles, foils, or marine blades. The average angle of each blade on the impeller relative to the drive shaft can be, identically or differently, any angle that facilitates the mixing of the solid particulate sample with the inert gas in the sample container such that a substantially fluidized bed of the solid particulates is formed. Examples of such angles include, but are not limited to, 0, 5, 10, 15, 20, 25, 30, 35, 40, 45, 50, 55, 60, 65, 70, 75, 80, and 85 degrees. In certain embodiments, two or more impellers are attached to the drive shaft such that the impellers are "stacked" on top of each other. The non-magnetic, electrically non-conductive impellers can be positioned in the sample container at any depth sufficient to facilitate mixing of the solid particulate sample with the inert gas in the sample container such that a substantially fluidized bed of the solid particulates is formed. This can be achieved by raising or lowering the non-magnetic, electrically non-conductive drive shaft inside the sample container. In certain embodiments, the substantially fluidized bed of the solid particulates can be formed in the sample container by the impeller's movement of the inert gas, by movement of the solid particulates via their direct contact with the impeller, or a combination of both. In certain embodiments, a flange can be incorporated into the portion of the non-magnetic, electrically non-conductive drive shaft located inside the sample container to prevent it from sliding out of the sample container while the sample undergoes NMR analysis. Examples of variable positioning of the non-magnetic, electrically non-conductive impeller and integration of a flange on the non-magnetic, electrically non-conductive drive shaft are illustrated in FIGS. 6A and 6B.

Any solid particulate samples of any average particle size can be analyzed using the devices of the present invention. In certain embodiments, the solid particulate sample is crystalline or an amorphous solid. In certain embodiments, the solid particulate sample is a powder. In certain embodiments, the average particle size of the solid particulate sample is 20 μM or less. Examples of average particle sizes of solid particulate samples that can be analyzed using the devices of the present invention include, but are not limited to, 20, 19, 18, 17, 16, 15, 14, 13, 12, 11, 10, 9, 8, 7, 6, 5, 4, 3, 2, and 1 μM. Any amount of solid particulate sample that is large enough to be analyzed by NMR spectroscopy but small enough to generate a substantially fluidized bed of solid particulates can be used in the devices of the present invention. In certain embodiments, the amount of solid particulate sample used is 200 mg or less. Examples of such amounts include, but are not limited to, 200, 199, 198, 197, 196, 195, 194, 193, 192, 191, 190, 189, 188, 187, 186, 185, 184, 183, 182, 181, 180, 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, and 1 mg. In other embodiments, the amount of solid particulate sample used is less than 10 g and greater than 200 mg. Examples of such amounts include, but are not limited to, 10, 9.5, 9, 8.5, 8, 7.5, 7, 6.5, 6, 5.5, 5, 4.5, 4, 3.5, 3, 2.5, 2, 1.5, 1, and 0.5 g.

The present disclosure is also directed methods for attenuating peak broadening in NMR analysis of a solid particulate sample using the devices described above. In certain embodiments, the methods comprise at least three steps: (1) providing a sample container with the solid particulate sample, (2) mixing the solid particulate sample with a non-magnetic, electrically non-conductive impeller rotated at a rate to generate a substantially fluidized bed of solid particulates, wherein a motor used to rotate the non-magnetic, electrically non-conductive impeller is air-driven, and (3) performing NMR analysis on the fluidized bed of solid particulates, as described above. In certain embodiments, step (2) of the above methods instead comprises mixing the solid particulate sample with a non-magnetic, electrically non-conductive impeller rotated at a rate to generate a substantially fluidized bed of solid particulates, wherein a motor used to rotate the non-magnetic, electrically non-conductive impeller is located at a distance from the sample container such that a magnetic field of a NMR spectrometer used to analyze the solid particulate sample in the sample container is about 0.5 millitesla or less at that distance.

From the above discussion, one skilled in the art can ascertain the essential characteristics of this invention, and without departing from the spirit and scope thereof, can make various changes and modifications of the invention to adapt it to various uses and conditions.

What is claimed is:

1. A device for attenuating peak broadening during NMR analysis of a solid particulate sample comprising:
   (A) a sample container having an inner wall and sized to hold the solid particulate sample;
   (B) a motor;
   (C) a non-magnetic, electrically non-conductive drive shaft having a first end and a second end, wherein the motor is fixably attached to the first end of the non-magnetic, electrically non-conductive drive shaft; and
   (D) a non-magnetic, electrically non-conductive impeller, wherein the non-magnetic, electrically non-conductive impeller is fixably attached to the second end of the non-magnetic, electrically non-conductive drive shaft and the non-magnetic impeller is located inside the sample container; wherein the motor is gas-driven.

2. A device for attenuating peak broadening during NMR analysis of a solid particulate sample comprising:
   (A) a sample container having an inner wall and sized to hold the solid particulate sample;
   (B) a motor;
   (C) a non-magnetic, electrically non-conductive drive shaft having a first end and a second end, wherein the motor is fixably attached to the first end of the non-magnetic, electrically non-conductive drive shaft; and
   (D) a non-magnetic, electrically non-conductive impeller, wherein the non-magnetic, electrically non-conductive impeller is fixably attached to the second end of the non-magnetic, electrically non-conductive drive shaft and the non-magnetic impeller is located inside the sample container; wherein the motor is magnetic and/or electrically-driven and is shielded from the NMR magnet.

3. The device of claim 2, wherein the shielding is active.

4. The device of claim 2, wherein the shielding is passive.

5. The device of claim 2, wherein the non-magnetic, electrically non-conductive shaft comprises carbon-filled PEEK.

6. A device for attenuating peak broadening during NMR analysis of a solid particulate sample comprising:
   (A) a sample container sized to hold the solid particulate sample;
   (B) a motor located at a distance from the sample container such that a magnetic field strength of a NMR magnet used to analyze the solid particulate sample in the sample container is about 0.5 millitesla or less at the distance;
   (C) a first and a second non-magnetic, electrically non-conductive drive shaft, wherein each non-magnetic, electrically non-conductive drive shaft has a first end and a second end, wherein (1) the motor is fixably attached to the first end of the first non-magnetic, electrically non-conductive drive shaft and (2) the first end of the second non-magnetic, electrically non-conductive drive shaft is fixably attached to the second end of the first non-magnetic, electrically non-conductive drive shaft through a transmission gear box; and
   (D) a non-magnetic, electrically non-conductive impeller fixably attached to the second end of the second non-magnetic, electrically non-conductive drive shaft, wherein the non-magnetic, electrically non-conductive impeller is located inside the sample container.

7. The device according to claim 6, wherein the transmission gear box comprises a 90 degree transmission gear box.

8. The device according to claim 6, wherein the motor drives the non-magnetic, electrically non-conductive impeller at a rate to generate a substantially fluidized bed of the solid particulate sample.

9. A device for attenuating peak broadening during NMR analysis of a solid particulate sample comprising:
   (A) a sample container sized to hold the solid particulate sample;
   (B) a motor located at a distance from the sample container, the distance selected such that substantially no disruption is caused to NMR analysis of the solid particulate sample;
   (C) a first and a second non-magnetic, electrically non-conductive drive shaft, wherein each non-magnetic, electrically non-conductive drive shaft has a first end and a second end, wherein (1) the motor is fixably attached to the first end of the first non-magnetic, electrically non-conductive drive shaft and (2) the first end of the second non-magnetic, electrically non-conductive drive shaft is fixably attached to the second end of the first non-magnetic, electrically non-conductive drive shaft through a transmission gear box; and
   (D) a non-magnetic, electrically non-conductive impeller fixably attached to the second end of the second non-magnetic, electrically non-conductive drive shaft, wherein the non-magnetic, electrically non-conductive impeller is located inside the sample container.

* * * * *